(12) United States Patent
Sekine

(10) Patent No.: US 11,033,502 B2
(45) Date of Patent: Jun. 15, 2021

(54) TABLET

(71) Applicant: DAIICHI SANKYO COMPANY, LIMITED, Tokyo (JP)

(72) Inventor: Kazuhisa Sekine, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/624,903

(22) PCT Filed: Jun. 26, 2018

(86) PCT No.: PCT/JP2018/024081
§ 371 (c)(1),
(2) Date: Dec. 19, 2019

(87) PCT Pub. No.: WO2019/004155
PCT Pub. Date: Jan. 3, 2019

(65) Prior Publication Data
US 2020/0113842 A1 Apr. 16, 2020

(30) Foreign Application Priority Data
Jun. 27, 2017 (JP) .............. JP2017-124904

(51) Int. Cl.
*A61K 9/20* (2006.01)
*A61K 9/28* (2006.01)
(52) U.S. Cl.
CPC .......... *A61K 9/2806* (2013.01); *A61K 9/2072* (2013.01)

(58) Field of Classification Search
CPC .... A61K 31/4178; A61K 31/444; A61K 9/20; A61K 9/2072; A61K 9/28; A61K 9/2806; A61P 7/02; A61P 9/12
See application file for complete search history.

(56) References Cited

U.S. PATENT DOCUMENTS 6,224,905 B1 * 5/2001 Lawrence ............ A61K 9/0056
424/464
6,270,790 B1 * 8/2001 Robinson ............ A61K 9/0056
424/441
(Continued)

FOREIGN PATENT DOCUMENTS

JP S62-141027 A 6/1987
JP 2002-332227 A 11/2002
(Continued)

OTHER PUBLICATIONS

Ansel et al. (Pharmaceutical Dosage Forms and Drug Delivery Systems 1999, 7th Ed. p. 222).2 pages (Year: 1999).*
(Continued)

*Primary Examiner* — Ernst V Arnold
(74) *Attorney, Agent, or Firm* — Foley & Lardner LLP

(57) ABSTRACT

The tablet of the present invention is a tablet 1 having a cup portion 12 formed at least above or below a side portion 11, wherein the outer surface of the cup portion 12 includes first, second and third curved surfaces 12a, 12b and 12c having different curvatures $R_1$, $R_2$ and $R_3$, the first curved surface 12a is at least continuous with the second curved surface 12b, the second curved surface 12b is continuous with the first curved surface 12a and the third curved surface 12c, and the third curved surface 12c is at least continuous with the second curved surface 12b.

20 Claims, 4 Drawing Sheets

(56) References Cited

U.S. PATENT DOCUMENTS

| | | | |
|---|---|---|---|
| 8,911,779 B2 | 12/2014 | Kitajima et al. | |
| 2006/0122194 A1 | 6/2006 | Berwaer et al. | |
| 2006/0165781 A1* | 7/2006 | Ferran ................. | A61K 9/0056 424/464 |
| 2009/0148520 A1 | 6/2009 | Arima et al. | |

FOREIGN PATENT DOCUMENTS

| | | |
|---|---|---|
| JP | 2006-510639 A | 3/2006 |
| JP | 3162325 U | 8/2010 |
| JP | 5564040 B2 | 7/2014 |
| JP | 5820847 B2 | 11/2015 |
| WO | WO-2010/032717 A1 | 3/2010 |
| WO | WO-2015/072442 A1 | 5/2015 |

OTHER PUBLICATIONS

Tsuda et al., "Basic lecture 10 for development of medicines: formulation engineering", Chijinshokan Co., Ltd., 1971, pp. 190-191.

Hibino et al., "Study on the Shape of Core Tablets for Sugar Coating Using Perforated Coating Machine", Research reports of the Mie Prefecture Industrial Research Institute, vol. 37, 2013, pp. 59-65.

International Searching Authority, "International Search Report," issued in connection with International Patent Application No. PCT/JP2018/024081, dated Aug. 7, 2018.

International Searching Authority, "Written Opinion," issued in connection with International Patent Application No. PCT/JP2018/024081, dated Aug. 7, 2018.

Extended European Search Report dated Feb. 18, 2021 for corresponding Patent Application No. 18822660.9.

Furukawa Ryoichi et al: "Numerical evaluation of the capping tendency of microcrystalline cellulose tablets during a diametrical compression test"; International Journal of Pharmaceutics; vol. 493, No. 1-2; Sep-Jan. 2015; pp. 182-191.

Harona Diarra et al: "Investigating the effect of tablet thickness and punch curvature on density distribution using finite elements method"; International Journal of Pharmaceutics; vol. 493, No. 1-2; Sep-Jan. 2015; pp. 121-128.

* cited by examiner

TABLET

CROSS-REFERENCE TO RELATED APPLICATIONS

The present application claims priority under 37 U.S.C. § 371 to International Patent Application No. PCT/JP2018/024081, filed Jun. 26, 2018, which claims priority to and the benefit of Japanese Patent Application No. 2017-124904, filed on Jun. 27, 2017. The contents of these applications are hereby incorporated by reference in their entireties.

TECHNICAL FIELD

The present invention relates to a tablet, and more particularly, relates to a tablet characterized by the shape thereof.

BACKGROUND ART

Typical tablets have the shape of a circle, oval, oblong shape, sphere, polygon or polyhedral and the like. In addition, there are also tablets having a shape in which the upper and lower sides bulge out to form a convex shape. The portion of the tablet that bulges out into a convex shape is generally referred to as the "cup portion". The outer surface of a conventional cup portion was composed of a curved surface having a single curvature or composed by combining a curved surface having a single curvature with a flat surface.

For example, JP 2002-332227 A (Patent Document 1) discloses a tablet in which is formed a cup portion comprised of a curved surface having a single curvature. JP 5564040 B2 (Patent Document 2) discloses a tablet in which the peripheral edge of the cup portion is comprised of an inclined flat surface and the central portion of the cup portion is comprised of a curved surface having a single curvature. JP 5820847 B2 (Patent Document 3) discloses a tablet in which the peripheral edge of the cup portion is comprised of a curved surface having a single curvature and the central portion of the cup portion is comprised of a horizontal flat surface.

PRIOR ART DOCUMENT

Patent Document
Patent Document 1: JP 2002-332227 A
Patent Document 2: JP 5564040 B2
Patent Document 3: JP 5820847 B2

SUMMARY OF THE INVENTION

Problems to be Solved by the Invention

Tablets are subjected to impacts and abrasion in various settings from production to administration resulting in the occurrence of defects (such as cracking, chipping or abrasion). For example, tablets are transported from the time they are compressed into tablets until the time they are packaged. In addition, after tablets have been shipped, they are dropped into automatic packaging machines at pharmacies. Moreover, tablets are pressed out of press through packs (PTP) when taken by a user. Tablets are subjected to impacts and abrasion resulting in damage in such various settings. For example, the cup portion of a tablet is easily damaged by impacts. In addition, the sides of tablets and the edges formed at the boundary with the cup portion are susceptible to damage by abrasion.

In order to prevent tablet damage, it is important to develop formulations that facilitate favorable tablet molding as well as suitably manage production parameters such as granulating conditions or tableting conditions.

However, even if evidence is obtained that a tablet has not been damaged at the research stage or testing stage, there are cases in which tablets end up being damaged in the actual production stage or during transport of the produced tablets. This is because, in the actual production stage, for example, there are cases in which tablets are subjected to strong impacts or subjected to different levels of tablet compression performance for each of a plurality of tableting machines. In addition, there are also cases in which tablets are subjected to unexpected impacts during the transport of produced tablets.

Therefore, the inventor of the present invention focused on a tablet having the configuration shown in FIG. 1 in order to develop a tablet having superior resistance to impacts and abrasion. FIG. 1 is a partially enlarged view showing half of a tablet in which the outer surface of the cup portion is comprised of two curved surfaces having different radii of curvature R (to also be referred to as "double-radius tablets").

As shown in FIG. 1, the double-radius tablet 100 employs a configuration in which a cup portion 102 is formed above and below side portions 101. The peripheral edge of the cup portion 102 is comprised of a first curved surface 102a having a radius of curvature $R_1$. The central portion of the cup portion 102 is comprised of a second curved surface 102b having a radius of curvature $R_2$. The radius of curvature $R_1$ is smaller than the radius of curvature $R_2$.

The double-radius tablet 100 includes the following shape parameters shown in FIG. 1. The following shape parameters are related to the occurrence of damage to the double-radius tablet 100:

a) rising angle α of the first curved surface 102a,
b) cup depth De,
c) tablet diameter (tablet diameter or major axis) TD,
d) radii of curvature $R_1$ and $R_2$, and
e) distance Di from inflection point P to side portion 101.

Furthermore, inflection point P of e) above refers to a point located at the boundary between the first curved surface 102a and the second curved surface 102b.

Here, FIGS. 2A and 2B is an overhead view showing a specific example of damage to the double-radius tablet 100. FIG. 2A indicates damage to the cup portion caused by an impact. FIG. 2B indicates damage to the edge caused by abrasion.

The inventor of the present invention repeatedly conducted tests on the double-radius tablet 100 by changing the aforementioned shape parameters. As a result, it was determined that damage to the cup portion 102 attributable to an impact (gray portion in FIG. 2A) occurred less likely the longer the distance Di, or in other words, the closer the location of the inflection point P was to the apex of the cup portion 102. However, even this double-radius tablet 100 had the problem of the occurrence of damage to the edge caused by abrasion (gray portion in FIG. 2B).

With the foregoing in view, an object of the present invention is to provide a tablet that has superior resistance to impacts and abrasion and is able to effectively prevent damage to the cup portion and edge.

Means for Solving the Problems (1) In order to achieve the aforementioned object, the tablet of the present invention is a tablet in which a cup portion is formed at least above or below a side portion, wherein a configuration is employed in which the outer surface of the cup portion includes first, second and third curved surfaces having different curvatures, the first curved surface is at least continuous with the second curved surface, the second curved surface is continuous with the first curved surface and the third curved surface, and the third curved surface is at least continuous with the second curved surface.

(2) Preferably, in the tablet of (1) above, the outer surface of the cup portion is only comprised of the first, second and third curved surfaces.

(3) Preferably, in the tablet of (1) or (2) above, a horizontal cross-section of the side portion is circular.

(4) Preferably, in the tablet of (1) or (2) above, a horizontal cross-section of the side portion has a shape other than that of a circle.

(5) Preferably, in the tablet of (4) above, a horizontal cross-section of the side portion is oval.

(6) Preferably, in the tablet of (4) above, a horizontal cross-section of the side portion is oblong.

(7) Preferably, in the tablet of any of (1) to (6) above, the value obtained by dividing the radius of curvature $R_2$ of the second curved surface by the radius of curvature $R_1$ of the first curved surface is within the range of 1.27 to 15.14.

(8) Preferably, in the tablet of (7) above, the value obtained by dividing the radius of curvature $R_2$ of the second curved surface by the radius of curvature $R_1$ of the first curved surface is within the range of 1.27 to 3.32.

(9) Preferably, in the tablet of (7) or (8) above, the value obtained by dividing the radius of curvature $R_3$ of the third curved surface by the radius of curvature $R_2$ of the second curved surface is within the range of 0.88 to 0.97.

(10) Preferably, in the tablet of any of (7) to (9) above, the value obtained by dividing the cup depth, which is the height dimension of the cup portion, by the diameter or long axis of the tablet is within the range of 0.14 to 0.18.

(11) Preferably, in the tablet of any of (7) to (10) above, the value obtained by dividing the distance from a first inflection point, which is the boundary between the first curved surface and the second curved surface, to an end of the side portion by the diameter or long axis of the tablet is within the range of 0.033 to 0.067.

(12) Preferably, in the tablet of any of (7) to (11) above, the value obtained by dividing the distance from a second inflection point, which is the boundary between the second curved surface and the third curved surface, to an end of the side portion by the diameter or long axis of the tablet is within the range of 0.33 to 0.34.

(13) Preferably, in the tablet of any of (7) to (12) above, the diameter or long axis is within the range of 6.0 mm to 10.5 mm.

(14) Preferably, in the tablet of any of (1) to (13) above, the apparent density of an uncoated tablet composing the tablet is within the range of 1.1 mg/mm³ to 1.4 mg/mm³.

(15) Preferably, in the tablet of any of (1) to (14) above, the surface of an uncoated tablet composing the tablet is coated.

(16) Preferably, in the tablet of (15) above, the surface of an uncoated tablet composing the tablet is coated with a film.

(17) Preferably, in the tablet of (7) or (8) above, the value obtained by dividing the radius of curvature $R_3$ of the third curved surface by the radius of curvature $R_2$ of the second curved surface is within the range of 0.75 to 0.97.

(18) Preferably, in the tablet of any of (7) to (9) above, the value obtained by dividing the cup depth, which is the height dimension of the cup portion, by the diameter or long axis of the tablet is within the range of 0.13 to 0.18.

(19) Preferably, in the tablet of any of (7) to (10) above, the value obtained by dividing the distance from a first inflection point located at the boundary between the first curved surface and the second curved surface to an end of the side portion by the diameter or long axis of the tablet is within the range of 0.030 to 0.067.

(20) Preferably, in the table of any of (7) to (11) above, the value obtained by dividing the distance from a second inflection point located at the boundary between the second curved surface and the third curved surface to an end of the side portion by the diameter or long axis of the tablet is within the range of 0.25 to 0.40.

(21) Preferably, in the tablet of any of (17) to (20) above, the diameter or long axis is within the range of 6.0 mm to 10.5 mm.

(22) Preferably, in the tablet of any of (17) to (21) above, the apparent density of an uncoated tablet composing the tablet is within the range of 1.1 mg/mm³ to 1.4 mg/mm³.

(23) Preferably, in the tablet of any of (17) to (22) above, the surface of an uncoated tablet composing the tablet is coated.

(24) Preferably, in the tablet of (23) above, the surface of an uncoated tablet composing the tablet is coated with a film.

(25) Preferably, in the tablet of any of (1) to (24) above, the tablet is an orally disintegrating tablet.

(26) Preferably, in the tablet of (1) above, the outer surface of the cup portion is comprised of the first, second, third and fourth curved surfaces.

(27) Preferably, in the tablet of (26) above, a horizontal cross-section of the side portion is circular.

(28) Preferably, in the tablet of (26) above, a horizontal cross-section of the side portion is a shape other than that of a circle.

(29) Preferably, in the tablet of (28) above, a horizontal cross-section of the side portion is oval.

(30) Preferably, in the tablet of (28) above, a horizontal cross-section of the tablet is oblong.

(31) Preferably, in the tablet of any of (26) to (30) above, the value obtained by dividing the radius of curvature $R_2$ of the second curved surface by the radius of curvature $R_1$ of the first curved surface is within the range of 1.27 to 15.14.

(32) Preferably, in the tablet of (31) above, the value obtained by dividing the radius of curvature $R_2$ of the second curved surface by the radius of curvature $R_1$ of the first curved surface is within the range of 1.27 to 3.32.

(33) Preferably, in the tablet of (31) or (32) above, the value obtained by dividing the radius of curvature $R_3$ of the third curved surface by the radius of curvature $R_2$ of the second curved surface is within the range of 0.88 to 0.97.

(34) Preferably, in the tablet of any of (31) to (33) above, the value obtained by dividing the cup depth, which is the height dimension of the cup portion, by the diameter or long axis of the tablet is within the range of 0.14 to 0.18.

(35) Preferably, in the tablet of any of (31) to (34) above, the value obtained by distance from a first inflection point, which is the boundary between the first curved surface and the second curved surface, to an end of the side portion by the diameter or long axis of the tablet is within the range of 0.033 to 0.067.

(36) Preferably, in the tablet of any of (31) to (35) above, the value obtained by dividing the distance from a second inflection point, which is the boundary between the second curved surface and the third curved surface, to an end of the side portion by the diameter or long axis of the tablet is within the range of 0.33 to 0.34.

(37) Preferably, in the tablet of any of (31) to (36) above, the diameter or long axis is within the range of 6.0 mm to 10.5 mm.

(38) Preferably, in the tablet of any of (26) to (37) above, the apparent density of an uncoated table composing the tablet is within the range of 1.1 mg/mm$^3$ to 1.4 mg/mm$^3$.

(39) Preferably, in the tablet of any of (26) to (38) above, the surface of an uncoated tablet composing the tablet is coated.

(40) Preferably, in the tablet of (39) above, the surface of an uncoated tablet composing the tablet is coated with a film.

(41) Preferably, in the tablet of any of (26) to (40) above, the tablet is an orally disintegrating tablet.

(42) Preferably, in the tablet of (31) or (32) above, the value obtained by dividing the radius of curvature $R_3$ of the third curved surface by the radius of curvature $R_2$ of the second curved surface is within the range of 0.75 to 0.97.

(43) Preferably, in the tablet of any of (31) to (33) above, the value obtained by dividing the cup depth, which is the height dimension of the cup portion, by the diameter or long axis of the tablet is within the range of 0.13 to 0.18.

(44) Preferably, in the tablet of any of (31) to (34) above, the value obtained by dividing the distance from a first inflection point located at the boundary between the first curved surface and the second curved surface to an end of the side portion by the diameter or long axis of the tablet is within the range of 0.030 to 0.067.

(45) Preferably, in the tablet of any of (31) to (35) above, the value obtained by dividing the distance from a second inflection point located at the boundary between the second curved surface and the third curved surface to an end of the side portion by the diameter or long axis of the tablet is within the range of 0.25 to 0.40.

(46) Preferably, in the tablet of any of (42) to (45) above, the diameter or long axis is within the range of 6.0 mm to 10.5 mm.

(47) Preferably, in the tablet of any of (42) to (46) above, the apparent density of an uncoated tablet composing the tablet is within the range of 1.1 mg/mm$^3$ to 1.4 mg/mm$^3$.

(48) Preferably, in the tablet of any of (42) to (47) above, the surface of an uncoated tablet composing the tablet is coated.

(49) Preferably, in the tablet of (48) above, the surface of an uncoated tablet composing the tablet is coated with a film.

(50) Preferably, in the tablet of any of (42) to (49) above, the tablet is an orally disintegrating tablet.

Effects of the Invention

According to the tablet of the present invention, resistance to impacts and abrasion is superior and damage to the cup portion and edge can be effectively prevented.

EMBODIMENTS TO CARRY OUT THE INVENTION

<Tablet Configuration>

The following provides an explanation of a tablet according to an embodiment of the present invention with reference to the drawings. Furthermore, the tablet of the present invention is not limited to the configuration of the embodiments and drawings explained below. For example, in the present embodiment, a tablet comprised of three curved surfaces having a different radius of curvature R for the outer surface of the cup portion (to be referred to as a "triple-radius tablet") is exemplified. However, the outer surface of the cup portion may also be composed by four or more curved surfaces each having a different radius of curvature R. In addition, the portion rising from the side portion of the cup portion may be a flat inclined surface. Moreover, the apex of the cup of the tablet may be a flat surface.

Figure 1:
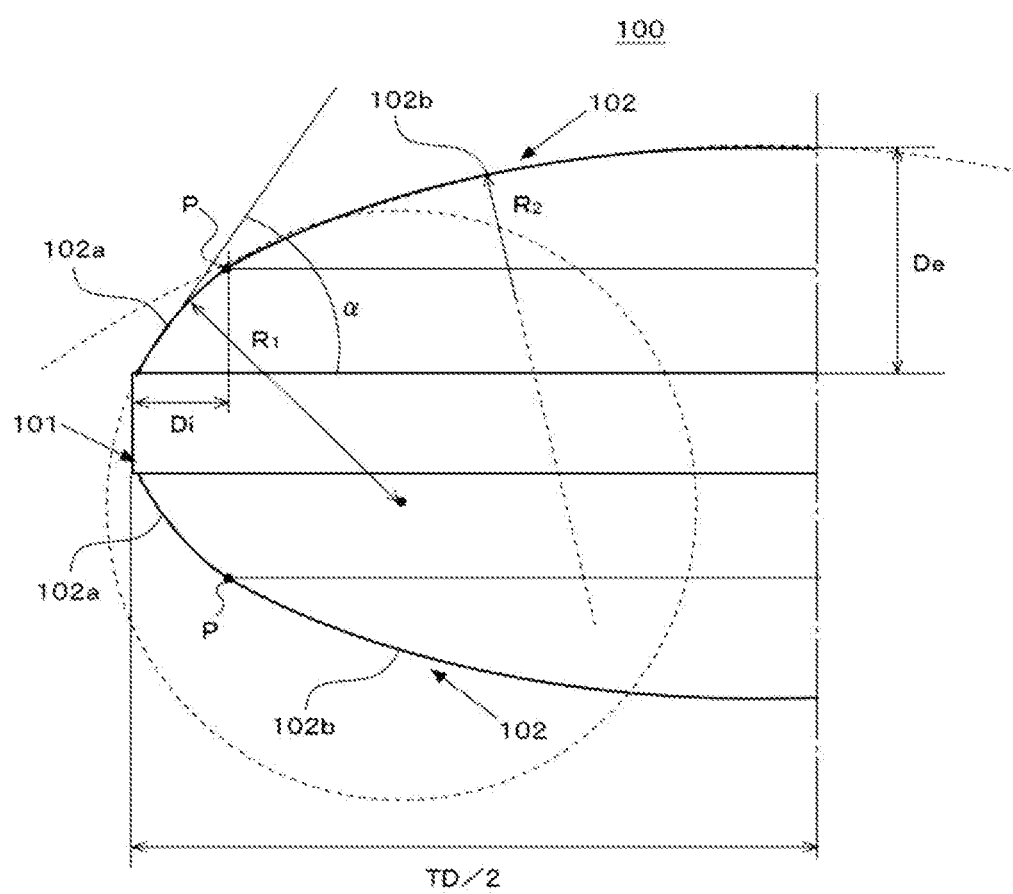
FIG. 1 is a partially enlarged view showing half of a double-radius tablet.
Figure 2A:
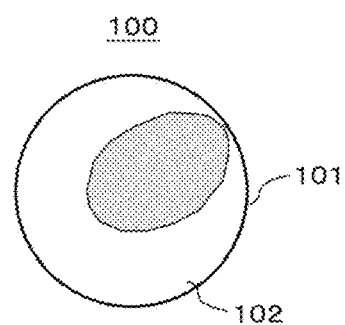
FIG. 2A is an overhead view showing damage to a cup portion caused by an impact.
Figure 2B:
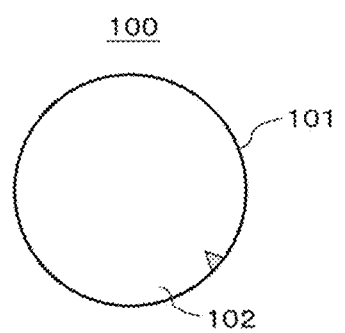
FIG. 2B is an overhead view showing damage to the edge caused by abrasion.
Figure 3:
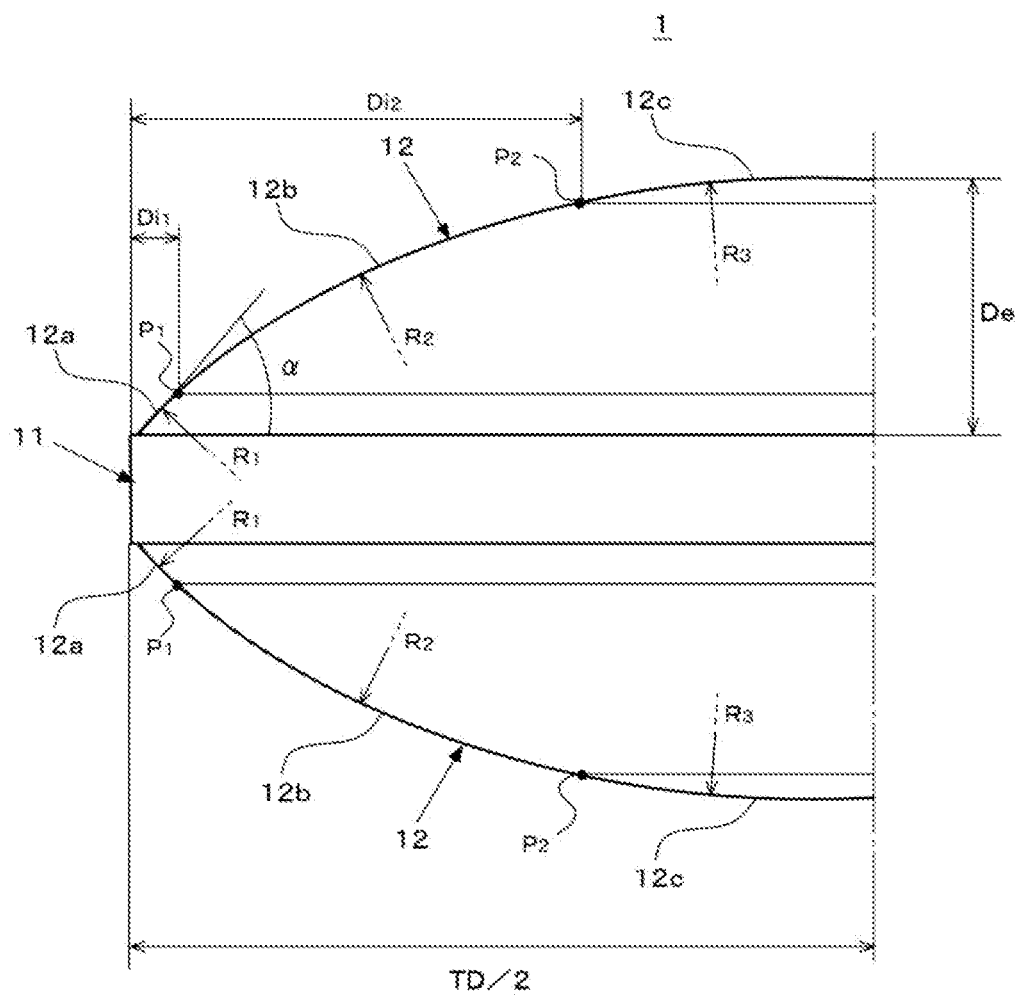
FIG. 3 is a partially enlarged view showing half of a triple-radius tablet according to an embodiment of the present invention.
Figure 4A:
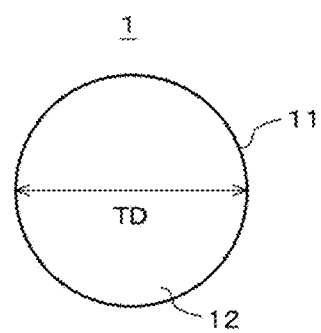
FIGS. 4A to 4D are overhead views showing specific examples of the shape of a triple-radius tablet.
Figure 4B:
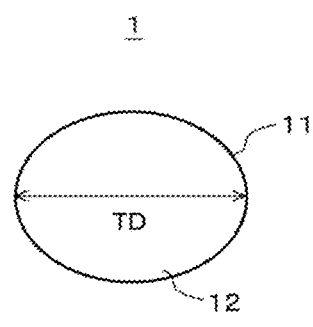
Figure 4C:
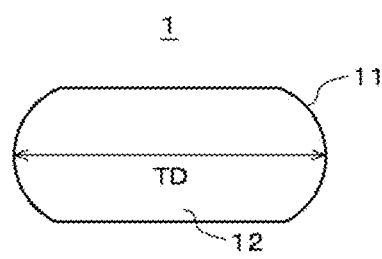
Figure 4D:
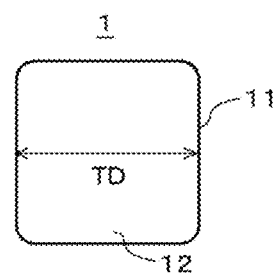

As shown in FIG. 3, a triple-radius tablet 1 of the present embodiment is composed by forming a cup portion 12 above and below a side portion 11. The outer surface of the cup portion 12 is comprised of a first curved surface 12a having a radius of curvature $R_1$, a second curved surface 12b having a radius of curvature $R_2$ and a third curved surface 12c having a radius of curvature $R_3$. Each radius of curvature $R_1$, $R_2$ and $R_3$ is mutually different.

The first curved surface 12a is continuous with the side portion 11 and the second curved surface 12b. The second curved surface 12b is continuous with the first curved surface 12a and the third curved surface 12c. The third curved surface 12c is only continuous with the second curved surface 12b and forms an apex located in the center of the triple-radius tablet 1.

The cup portion 12 of the triple-radius tablet 1 has first and second inflection points $P_1$ and $P_2$. The first inflection point $P_1$ is located at the boundary between the first curved surface 12a and the second curved surface 12b. The second inflection point $P_2$ is located at the boundary between the second curved surface 12b and the third curved surface 12c.

Here, there are no particular limitations on the shape of the triple-radius tablet 1 when viewed from overhead. For example, as shown in FIGS. 4A to 4D, the shape of the triple-radius tablet 1 may be circular, oval, oblong or polygonal such as triangular, quadrangular, pentagonal, hexagonal or rhomboid.

<Setting of Shape Parameters>

The triple-radius tablet 1 includes the following shape parameters shown in FIG. 3:

A) rising angle α of the first curved surface 12a,
B) cup depth De,
C) tablet diameter (tablet diameter or major axis) TD,
D) radii of curvature $R_1$, $R_2$ and $R_3$,
E) distance $Di_1$ from the first inflection point $P_1$ to an end of the side portion 11 (provided the distance $Di_1$ is the shorter distance of the distances from the first inflection point $P_1$ to the two ends of the side portion 11), and
F) distance $Di_2$ from the second inflection point $P_2$ to an end of the side portion 11 (provided the distance $Di_2$ is the shorter distance of the distances from the second inflection point $P_2$ to the two ends of the side portion 11).

The triple-radius tablet 1 demonstrates superior resistance to impacts and abrasion by setting the aforementioned shape parameters to suitable values. The following indicates an example of preferable set values for the aforementioned shape parameters.

The value obtained by dividing the radius of curvature $R_2$ of the second curved surface 12b by the radius of curvature $R_1$ of the first curved surface 12a is preferably set to be within a range of 1.27 to 15.14 (Setting 1). More preferably, the value obtained by dividing the radius of curvature $R_2$ of the second curved surface 12b by the radius of curvature $R_1$ of the first curved surface 12a is set to be within the range of 1.27 to 4.18. Even more preferably, the value obtained by dividing the radius of curvature $R_2$ of the second curved surface 12b by the radius of curvature $R_1$ of the first curved surface 12a is set to be within the range of 1.27 to 3.32.

The value obtained by dividing the radius of curvature $R_3$ of the third curved surface 12c by the radius of curvature $R_2$ of the second curved surface 12b is preferably set to be within the range of 0.75 to 0.97 (Setting 2). More preferably, the value obtained by dividing the radius of curvature $R_3$ of the third curved surface 12c by the radius of curvature $R_2$ of the second curved surface 12b is set to be within the range of 0.88 to 0.97. Even more preferably, the radii of curvature $R_1$, $R_2$ and $R_3$ satisfy both of the aforementioned Settings 1 and 2.

The value obtained by dividing the cup depth De, which is the height dimension of the cup portion 12, by the diameter or long axis of the triple-radius tablet 1 is preferably set to be within the range of 0.13 to 0.18 (Setting 3). More preferably, the value obtained by dividing the cup depth De, which is the height dimension of the cup portion 12, by the diameter or long axis of the triple-radius tablet 1 is set to be within the range of 0.14 to 0.18.

The value obtained by dividing the distance $Di_1$ from the first inflection point $P_1$ to an end of the side portion 11 by the diameter or long axis of the triple-radius tablet 1 is preferably set to be within the range of 0.01 to 0.09 (Setting 4). More preferably, the value obtained by dividing the distance $Di_1$ from the first inflection point $P_1$ to an end of the side portion 11 by the diameter or long axis of the triple-radius tablet 1 is set to be within the range of 0.030 to 0.067. Even more preferably, the value obtained by dividing the distance $Di_1$ from the first inflection point $P_1$ to an end of the side portion 11 by the diameter or long axis of the triple-radius tablet 1 is set to be within the range of 0.033 to 0.067.

The value obtained by dividing the distance $Di_2$ from the second inflection point $P_2$ to an end of the side portion 11 by the diameter or long axis of the triple-radius tablet 1 is preferably set to be within the range of 0.25 to 0.40 (Setting 5). More preferably, the value obtained by dividing the distance $Di_2$ from the second inflection point $P_2$ to an end of the side portion 11 by the diameter or long axis of the triple-radius tablet 1 is set to be within the range of 0.33 to 0.40. Even more preferably, the first and second inflection points $P_1$ and $P_2$ satisfy both of the aforementioned Settings 4 and 5.

The diameter or long axis of the triple-radius tablet 1 is preferably set to be within the range of 6.0 mm to 10.5 mm (Setting 6).

The aforementioned Settings 1 to 6 all affect the resistance of the triple-radius tablet 1 to impacts and abrasion. By applying one or more of the aforementioned Settings 1 to 6 to the shape parameters of the triple-radius tablet 1, resistance of the triple-radius tablet 1 to impacts and abrasion is improved. By applying all of the aforementioned Settings 1 to 6 to the shape parameters of the triple-radius tablet 1, the triple-radius tablet 1 demonstrates superior resistance to impacts and abrasion.

Moreover, the apparent density of an uncoated tablet composing the triple-radius tablet 1 is preferably set to be within the range of 1.1 mg/mm$^3$ to 1.4 mg/mm$^3$ (Setting 7). More preferably, the apparent density of an uncoated tablet composing the triple-radius tablet 1 is set to be within the range of 1.14 mg/mm$^3$ to 1.32 mg/mm$^3$.

<Tablet Production>

The triple-radius tablet 1 of the present embodiment is produced by a tableting machine provided with a die provided with a cylinder and a pair of upper and lower punches. Triple-radius concave portions for molding the cup portion 12 are provided in the pair of upper and lower punches. The side portion 11 is molded by the inner peripheral surface of the cylinder of the die. A powdered preparation is placed in the cylinder of the die followed by compressing and molding this powdered preparation with the pair of upper and lower punches. The triple-radius tablet 1 is produced as a result thereof.

<Tablet Abrasion Resistance Performance>

Abrasion resistance of the triple-radius tablet 1 can be measured with a commercially available friability tester. A friability tester calculates friability of a tablet by vibrating or rotating a container in which a plurality of tablets have been placed. A plurality of uncoated tablets is used in the friability test. These uncoated tablets are placed in the container of the friability tester after having precisely measured the weight thereof. Subsequently, the container is vibrated or rotated. After having completed vibrating or rotating the container, the weight of all of the uncoated tablets is precisely measured to calculate friability (percentage of reduced weight to initial weight).

Friability of the triple-radius tablet 1 can be made to be from 3% to 1% or less according to the settings of the aforementioned shape parameters (refer to the "Examples" to be subsequently described). For example, friability is preferably 3% or less in the case the triple-radius tablet 1 is an orally disintegrating tablet.

<Tablet Impact Resistance Performance>

Impact resistance performance of the triple-radius tablet 1 can be measured by a drop test. A drop test consists of dropping the triple-radius tablet 1 from a prescribed height and measuring the height at which cracking or chipping does not occur (refer to the "Examples" to be subsequently described). Impact resistance performance of the triple-radius tablet 1 is determined based on the status thereof at each of the stages of production, distribution, sales and consumption. For example, there are cases in which the triple-radius tablet 1 is dropped from a high location by a lifter in the production stage. In such cases, impact resistance performance such that cracking or chipping does not occur even if dropped from a height of about 200 cm is preferably imparted to the triple-radius tablet 1. In addition, there are cases in which the triple-radius tablet 1 is dropped within an automatic packing machine at a pharmacy. In such cases, impact resistance performance such that cracking or chipping does not occur even if dropped from a height of about 130 cm is preferably imparted to the triple-radius tablet 1. Moreover, in cases in which the triple-radius tablet 1 is not dropped from a high location in any of the production, distribution or sales stages, impact resistance performance such that cracking or chipping does not occur even if dropped from a height of about 50 cm is imparted to the triple-radius tablet 1. Furthermore, in the case the triple-radius tablet 1 is an orally disintegrating tablet, impact resistance performance on the order of about 50 cm or about 130 cm is imparted to the triple-radius tablet 1.

<Tablet Composition>

The triple-radius tablet 1 of the present embodiment is characterized by the shape thereof. Thus, there are no particular limitations on the preparation raw material of the triple-radius tablet 1, and the characteristic shape of the triple-radius tablet 1 can be broadly applied to ordinary preparation raw materials.

There are also no particular limitations on the pharmaceutical active ingredient contained in the triple-radius tablet 1 of the present embodiment. For example, a crystalline or amorphous solid pharmaceutical active ingredient can be contained in the triple-radius tablet 1.

<Tablet Production Method>

There are no particular limitations on the production method of the triple-radius tablet 1 of the present embodiment, and can be produced according to the same production method as that used to produce ordinary tablets. For example, the characteristic shape of the triple-radius tablet 1 can be formed with a tableting machine. Furthermore, although there are no particular limitations thereon, the weight of the produced triple-radius tablet 1 is preferably within the range of 80 mg to 500 mg and more preferably within the range of 80 mg to 400 mg.

<Tablet Coating>

The characteristic shape of the triple-radius tablet 1 of the present embodiment can be applied to a coated tablet or uncoated tablet, and demonstrates superior resistance to impacts and abrasion. A coating of the triple-radius tablet 1 may be any of a film coating, sugar coating or enteric coating and the like, and there are no particular limitations thereon.

EXAMPLES

The following provides an explanation of examples of the tablet of the present invention. Furthermore, the present invention is not limited to the examples explained below, and the wording of the claims should not in any sense be interpreted as being limiting.

<Formulation>

Each of the tablets of the examples and comparative examples was produced in accordance with Formulations 1 to 3 of the following Tables 1 to 3. The ratios of the formulations listed in each table are indicated as percent by weight (wt/%).

TABLE 1

<Formulation 1>

| Component Name | Ratio (%) |
|---|---|
| Olmesartan medoxomil | 12.5 |
| Low substituted hydroxypropyl cellulose | 12.5 |
| Hydroxypropyl cellulose | 1.9 |
| Crystalline cellulose | 6.3 |
| Lactose | 66.3 |
| Magnesium stearate | 0.6 |

Olmesartan medoxomil, lactose, low substituted hydroxypropyl cellulose and hydroxypropyl cellulose were primarily mixed with a high-speed stirring granulator followed by the addition of purified water, kneading and granulating the resulting granules. After having dried the granulated granules with a fluidized bed dryer, the granules were sized to have a uniform size. Crystalline cellulose and magnesium stearate were added to the resulting granules followed by secondary mixing to obtain granules for tableting. Subsequently, the granules for tableting were tableted to produce uncoated tablets.

TABLE 2

<Formulation 2>

| Component Name | Ratio (%) |
|---|---|
| Edoxaban tosilate hydrate | 20.2 |
| D-mannitol | 49.6 |
| Pregelatinized starch | 21.0 |
| Crospovidone | 5.4 |
| Hydroxypropyl cellulose | 3.1 |
| Magnesium stearate | 0.8 |

Edoxaban tosilate hydrate, D-mannitol, pregelatinized starch and crospovidone were placed in a fluidized bed granulator and granulated using aqueous hydroxypropyl cellulose solution. The resulting granules and magnesium stearate were mixed to obtain granules for tableting. The resulting granules for tableting were tableted to produce uncoated tablets.

TABLE 3

<Formulation 3>

| Component Name | Ratio (%) |
|---|---|
| D-mannitol | 98.0 |
| Magnesium stearate | 2.0 |

D-mannitol and magnesium stearate were mixed to obtain a tableting mixed powder. The resulting tableting mixed powder was tableted to produce uncoated tablets.

<Configuration of Each Tablet>

The following Table 4 indicates the configuration of each tablet of the examples and comparative examples. Each tablet had a circular shape when viewed from overhead (see FIG. 4A) and was produced according to an ordinary production method.

TABLE 4

| | Formulation | Cup portion | TD (mm) | TW (mg) | De (mm) | $Di_1/TD$ | $Di_2/TD$ | $R_2/R_1$ | $R_3/R_2$ | De/TD |
|---|---|---|---|---|---|---|---|---|---|---|
| Example 1-1 | 1 | Triple radius | 10.6 | 400 | 1.50 | 0.052 | 0.34 | 3.32 | 0.88 | 0.14 |
| Example 1-2 | 2 | | | | | | | | | |
| Example 1-3 | 3 | | | | | | | | | |
| Example 2 | 3 | | 6 | 80 | 0.86 | 0.053 | 0.34 | 1.62 | 0.97 | 0.14 |
| Example 3 | | | | | 0.83 | 0.067 | 0.34 | 3.14 | 0.90 | 0.14 |
| Example 4 | | | | | 1.06 | 0.053 | 0.34 | 1.27 | 0.97 | 0.18 |
| Example 5 | | | | | 0.88 | 0.033 | 0.33 | 15.14 | 0.92 | 0.15 |
| Example 6 | | | 10.6 | 400 | 1.50 | 0.053 | 0.40 | 3.32 | 0.82 | 0.14 |
| Example 7 | | | | | 1.50 | 0.052 | 0.25 | 3.25 | 0.91 | 0.14 |
| Example 8 | | | | | 1.50 | 0.052 | 0.28 | 4.18 | 0.75 | 0.14 |
| Example 9 | | | | | 1.40 | 0.030 | 0.38 | 10.26 | 0.92 | 0.13 |
| Comparative Example 1-1 | 1 | Double radius | 10.6 | 400 | 1.50 | 0.098 | — | 2.04 | 1.00 | 0.14 |
| Comparative Example 1-2 | 2 | | | | | | | | | |
| Comparative Example 1-3 | 3 | | | | | | | | | |
| Comparative Example 2-1 | 1 | Single radius | 10.6 | 400 | 1.42 | — | — | 1.00 | 1.00 | 0.14 |
| Comparative Example 2-2 | 2 | | | | | | | | | |

TABLE 4-continued

| | Formulation | Cup portion | TD (mm) | TW (mg) | De (mm) | $Di_1$/TD | $Di_2$/TD | $R_2/R_1$ | $R_3/R_2$ | De/TD |
|---|---|---|---|---|---|---|---|---|---|---|
| Comparative Example 2-3 | 3 | | | | | | | | | |
| Comparative Example 3 | 3 | Double radius | 6 | 80 | 1.00 | 0.153 | — | 4.39 | 1.00 | 0.17 |
| Comparative Example 4 | | | | | 0.75 | 0.090 | | | | 0.13 |

In Table 4, TD (mm) represents tablet diameter, TW (mg) represents tablet weight, De (mm) represents cup depth, $Di_1$ represents the distance from the first inflection point $P_1$ to an end of the side portion, $Di_2$ represents the distance from the second inflection point $P_2$ to an end of the side portion, $R_1$ represents the radius of curvature of the first curved surface, $R_2$ represents the radius of curvature of the second curved surface, and $R_3$ represents the radius of curvature of the third curved surface. In addition, the value of tablet diameter TD and tablet weight TW in Table 4 indicate the size of the tablet. Namely, a tablet diameter TD of 10.5 mm and a tablet weight TW of 400 mg indicate that the examples and comparative examples constitute large tablets. A tablet diameter TD of 6 mm and tablet weight TW of 80 mg indicates that the examples and comparative examples constitute small tablets.

<Friability Test Conditions>

Ten tablets having the same configuration were used in the friability test. After measuring the initial weight of the 10 tablets, the tablets were placed in a plastic syringe. The syringe consisted of a cylinder having a diameter of about 2 cm and length of about 7 cm. The syringe was vibrated about 20 cm in the longitudinal direction for 2 minutes at 250 times/minute with a vibrator. Following completion of vibration of the syringe with the vibrator, the reduced weights of the 10 tablets were measured. Friability (%) was calculated based on the initial weight and reduced weight of the ten tablets.

<Drop Test Conditions>

The drop test was carried out on one tablet at a time using 5 tablets having the same configuration. Each tablet was fit onto the end of a probe, and the probe was allowed to free fall in the vertical direction along a guide and collide with a metal plate. The probe consisted of a plastic cylinder having a diameter of about 2 cm, length of about 15 cm and weight of about 23 g. The end of the probe was provided with an indentation for engaging with a tablet. The appearance of each tablet that underwent the drop test was observed and tablets observed to contain a chip of 1 $mm^2$ or more were determined to be unacceptable. A drop test on a single tablet was carried out repeatedly while increasing the drop height of the probe in 5 mm increments, and was completed at the point the tablet was determined to be unacceptable. The maximum value of drop height at which all five tablets were not determined to be unacceptable was recorded as the "actual drop height". Since the value of "actual drop height" is affected by the weight of the probe, the value was corrected according to the following equation (1) to calculate the value of "equivalent drop height" for when the tablet was allowed to drop independently.

Equivalent drop height=actual drop height×(tablet weight+probe weight)/tablet weight (1)

Weight units are in mg and height units are in cm.

<Measurement of Tablet Hardness>

Ten tablets having the same configuration were used to measure tablet hardness. The hardness of the 10 tablets was measured using a fully automated tablet testing instrument (WHT-3MJ) manufactured by Pharma Test GmbH.

<Physical Property Evaluation Results 1>

The following Table 5 indicates the results of evaluating physical properties of triple-radius tablets of Examples 1-1, 1-2 and 1-3 and double-radius tablets of Comparative Examples 1-1, 1-2 and 1-3. The tablets of Example 1-1 and Comparative Example 1-1, Example 1-2 and Comparative Example 1-2, and Example 1-3 and Comparative Example 1-3 were respectively produced according to the same Formulations 1 to 3. The tablets of all of the examples and comparative examples shown in Table 5 have the same tablet diameter TD (mm), tablet weight TW (mg), cup depth De (mm) and rising angle α.

TABLE 5

| Shape | Example 1-1 | Comparative Example 1-1 | Example 1-2 | Comparative Example 1-2 | Example 1-3 | Comparative Example 1-3 |
|---|---|---|---|---|---|---|
| Formulation | 1 | | 2 | | 3 | |
| Cup portion | Triple radius | Double radius | Triple radius | Double radius | Triple radius | Double radius |
| Tablet density (mg/$mm^3$) | 1.26 | 1.27 | 1.14 | 1.14 | 1.27 | 1.27 |
| Tablet hardness (N) | 5.9 | 6.1 | 5.7 | 5.5 | 19.6 | 19.6 |
| Friability (%) | 1.2 | 1.2 | 1.7 | 1.9 | 2.5 | 2.3 |
| Equivalent drop height (cm) | 61 | 53 | 98 | 73 | 124 | 90 |

The friability (%) of Examples 1-1, 1-2 and 1-3 exhibited equivalent values to that of Comparative Examples 1-1, 1-2 and 1-3. This result indicates that the triple-radius shape of Examples 1-1, 1-2 and 1-3 demonstrates abrasion resistance performance equivalent to that of the double-radius shape of Comparative Examples 1-1, 1-2 and 1-3.

On the other hand, tablet strength is related to rising angle α of the first curved surface of the cup portion and cup depth De (Patent Document 1). As was previously described, the tablets of all of the examples and comparative examples shown in Table 5 have the same rising angle α and cup depth De. The equivalent drop height (cm) of Examples 1-1, 1-2 and 1-3 is higher than the equivalent drop height (cm) of each of Comparative Examples 1-1, 1-2 and 1-3. This result indicates that the triple-radius shape of Examples 1-1, 1-2 and 1-3 demonstrates impact resistance performance that is superior to that of the double-radius shape of the comparative examples.

As has been described above, as a result of employing a triple-radius shape for the cup portion of the tablet, abrasion resistance performance was confirmed to be demonstrated that it is equivalent to a double-radius shape, and impact resistance performance was confirmed to be demonstrated that it is superior to that of the double-radius shape.

<Physical Property Evaluation Results 2>

The following Table 6 indicates the results of evaluating the physical properties of triple-radius tablets of Examples 1-1, 1-2 and 1-3 and single-radius tablets of Comparative Examples 2-1, 2-2 and 2-3. The tablets of Example 1-1 and Comparative Example 2-1, Example 1-2 and Comparative Example 2-2, and Example 1-3 and Comparative Example 2-3 were respectively produced according to the same Formulations 1 to 3. Although the tablets of all of the examples and comparative examples shown in Table 6 have the same tablet diameter TD (mm) and tablet weight TW (mg), the cup depth De (mm) thereof is mutually different.

TABLE 6

| Shape | Example 1-1 | Comparative Example 2-1 | Example 1-2 | Comparative Example 2-2 | Example 1-3 | Comparative Example 2-3 |
| --- | --- | --- | --- | --- | --- | --- |
| Formulation | 1 | | 2 | | 3 | |
| Cup portion | Triple radius | Single radius | Triple radius | Single radius | Triple radius | Single radius |
| Tablet density (mg/mm$^3$) | 1.22 | 1.21 | 1.23 | 1.24 | 1.21 | 1.22 |
| Tablet hardness (N) | 4.3 | 3.9 | 10.5 | 11.0 | 15.7 | 16.4 |
| Friability (%) | 2.8 | 4.2 | 0.7 | 0.7 | 1.4 | 1.5 |
| Equivalent drop height (cm) | 61 | 42 | 146 | 131 | 115 | 92 |

The friability (%) of Examples 1-1, 1-2 and 1-3 exhibited equivalent values to that of Comparative Examples 2-1, 2-2 and 2-3. This result indicates that the triple-radius shape of Examples 1-1, 1-2 and 1-3 demonstrates abrasion resistance performance equivalent to that of the single-radius shape of Comparative Examples 2-1, 2-2 and 2-3.

On the other hand, the equivalent drop height (cm) of Examples 1-1, 1-2 and 1-3 is higher than the equivalent drop height (cm) of each of Comparative Examples 2-1, 2-2 and 2-3. This result indicates that the triple-radius shape of Examples 1-1, 1-2 and 1-3 demonstrates impact resistance performance that is superior to that of the single-radius shape of Comparative Examples 2-1, 2-2 and 2-3.

As has been described above, as a result of employing a triple-radius shape for the cup portion of the tablet, abrasion resistance performance was confirmed to be demonstrated that it is equivalent to a single-radius shape, and impact resistance performance was confirmed to be demonstrated that it is superior to that of the single-radius shape.

<Physical Property Evaluation Results 3>

The following Table 7 indicates the results of evaluating the physical properties of the triple-radius tablets of Examples 2, 3, 4 and 5 and the double-radius tablets of Comparative Examples 3 and 4. All of the tablets of the examples and comparative examples were produced according to the same Formulation 3 and have the same tablet diameter TD (mm) and tablet weight TW (mg). The tablets of Examples 2, 3, 4 and 5 and the tablet of Comparative Example 3 have mutually different cup depths De (mm). Moreover, the tablets of Example 3 and Comparative Example 4 have the same cup depth De (mm). Moreover, all of the tablets of the examples and comparative examples shown in Table 7 have mutually different curved surfaces of the cup portion ($R_2/R_1$ and $R_3/R_2$ in Table 4).

TABLE 7

| Shape | Example 2 | Example 3 | Example 4 | Example 5 | Comparative Example 3 | Comparative Example 4 |
| --- | --- | --- | --- | --- | --- | --- |
| Formulation | | | | 3 | | |
| Cup portion | Triple radius | | | | Double radius | |
| Tablet density (mg/mm$^3$) | 1.29 | 1.29 | 1.30 | 1.29 | 1.30 | 1.30 |
| Tablet hardness (N) | 8.2 | 8.5 | 7.1 | 8.6 | 5.2 | 9.8 |
| Friability (%) | 1.1 | 1.1 | 0.8 | 1.0 | 0.6 | 1.2 |
| Equivalent drop height (cm) | 252 | 242 | 240 | 286 | 166 | 181 |

The friability (%) of Examples 2, 3, 4 and 5 exhibited equivalent values to those of Comparative Examples 3 and 4. This result indicates that the triple-radius shape of Examples 2, 3, 4 and 5 demonstrates abrasion resistance performance equivalent to that of the double-radius shape of Comparative Examples 3 and 4 despite differences in the cup depth De (mm) and curved shape of the cup portion.

On the other hand, the equivalent drop height (cm) of Examples 2, 3, 4 and 5 is considerably higher than the equivalent drop height (cm) of each of Comparative Examples 3 and 4. This result indicates that the triple-radius shape of Examples 2, 3, 4 and 5 demonstrates impact resistance performance that is superior to that of the double-radius shape of Comparative Examples 3 and 4 despite differences in the cup depth De (mm) and curved shape of the cup portion.

Here, all of the tablets of the examples and comparative examples shown in Table 7 are small tablets having a tablet diameter TD (mm) of 6 mm (see Table 4). The evaluation results of Table 7 indicate that, even in the case of tablets having a small tablet diameter TD (mm), the triple-radius shape that satisfies the parameters of Table 4 demonstrates abrasion resistance performance equivalent to that of the double-radius shape and demonstrates impact resistance performance that is superior to the double-radius shape.

<Physical Property Evaluation Results 4>

The following Table 8 indicates the results of evaluating the physical properties of the triple-radius tablets of Examples 6, 7, 8 and 9 and the double-radius tablet of Comparative Example 1-3. All of the tablets of the examples and comparative examples were produced according to the same Formulation 3 and have the same tablet diameter TD (mm) and tablet weight TW (mg). Although the tablets of Examples 6, 7 and 8 have the same cup depth De (mm) as that of Comparative Example 1-3, the tablet of Example 9 has a different cup depth De (mm) from that of Comparative Example 1-3. Moreover, all of the tablets of the examples and comparative examples shown in Table 8 have mutually different curved surfaces of Here, all of the tablets of the examples and comparative examples shown in Table 8 are large tablets having a tablet diameter TD (mm) of 10.5 mm (see Table 4). The evaluation results of Table 8 indicate that, even in the case of tablets having a large tablet diameter TD (mm), the triple-radius shape that satisfies the parameters of Table 4 demonstrates abrasion resistance performance equivalent to that of the double-radius shape and demonstrates impact resistance performance that is superior to the double-radius shape.

<Summary>

When comprehensively considering the friability shown in Tables 5, 6, 7 and 8, the triple-radius tablets of all of the examples can be understood to demonstrate abrasion resistance performance that is equivalent to all of the single-radius and double-radius tablets of the comparative examples despite differences in tablet diameter TD (mm) and tablet weight TW (g).

In addition, when comprehensively considering the equivalent drop height (cm) shown in Tables 5, 6, 7 and 8, the triple-radius tablets of all of the examples can be understood to demonstrate impact resistance performance that is superior to all of the single-radius and double-radius tablets of the comparative examples. In particular, the triple-radius tablets satisfying the parameters of Table 4 demonstrate abrasion resistance performance equivalent to that of double-radius tablets and impact resistance performance that is superior to that of double-radius tablets regardless of the size of tablet diameter TD (mm).

As has been described above, the triple-radius tablet of the present invention represented in the examples demonstrates abrasion resistance performance equivalent to that of single-radius and double-radius tablets and demonstrates impact resistance performance that is superior to single-radius and double-radius tablets in terms of the various Formulations 1 to 3, tablet diameter TD (mm), tablet weight TW (g), cup depth De (mm) and curved shape of the cup portion.

TABLE 8

| Shape | Example 6 | Example 7 | Example 8 | Example 9 | Comparative Example 1-3 |
|---|---|---|---|---|---|
| Formulation | | | 3 | | |
| Radius | | Triple radius | | | Double radius |
| Tablet density (mg/mm$^3$) | 1.31 | 1.32 | 1.31 | 1.32 | 1.32 |
| Tablet hardness (N) | 22.4 | 22.6 | 25.5 | 27.4 | 27.3 |
| Friability (%) | 1.4 | 1.7 | 1.3 | 1.7 | 1.3 |
| Equivalent drop height (cm) | 63 | 69 | 132 | 128 | 46 |

The friability (%) of Examples 6, 7, 8 and 9 exhibited equivalent values to that of the friability (%) of Comparative Example 1-3. This result indicates that the triple-radius shape of Examples 6, 7, 8 and 9 demonstrates abrasion resistance performance equivalent to that of the double-radius shape of Comparative Example 1-3 despite differences in the cup depth De (mm) and curved shape of the cup portion.

On the other hand, the equivalent drop height (cm) of Examples 6, 7, 8 and 9 is considerably higher than that of Comparative Example 1-3. This result indicates that the triple-radius shape of Examples 6, 7, 8 and 9 demonstrates impact resistance performance that is superior to that of the double-radius shape of Comparative Example 1-3 despite differences in the cup depth De (mm) and curved shape of the cup portion.

BRIEF DESCRIPTION OF THE REFERENCE SYMBOLS

1 Tablet (triple-radius tablet)
11 Side portion
12 Cup portion
12a First curved surface
12b Second curved surface
12c Third curved surface

The invention claimed is:

1. A tablet in which a cup portion is formed at least above or below a side portion, wherein
the outer surface of the cup portion includes first, second and third curved surfaces having different curvatures,
the first curved surface is at least continuous with the second curved surface, the second curved surface is continuous with the first curved surface and the third curved surface, the third curved surface is at least continuous with the second curved surface, the value obtained by dividing the radius of curvature $R_2$ of the second curved surface by the radius of curvature $R_1$ of the first curved surface is within the range of 1.27 to 15.14, and the value obtained by dividing the radius of curvature $R_3$ of the third curved surface by the radius of curvature $R_2$ of the second curved surface is within the range of 0.75 to 0.97.

2. The tablet according to claim 1, wherein the outer surface of the cup portion is only comprised of the first, second and third curved surfaces.

3. The tablet according to claim 1, wherein a horizontal cross-section of the side portion is circular.

4. The tablet according to claim 1, wherein a horizontal cross-section of the side portion has a shape other than that of a circle.

5. The tablet according to claim 4, wherein a horizontal cross-section of the side portion is oval.

6. The tablet according to claim 4, wherein a horizontal cross-section of the side portion is oblong.

7. The tablet according to claim 1, wherein the value obtained by dividing the radius of curvature $R_2$ of the second curved surface by the radius of curvature $R_1$ of the first curved surface is within the range of 1.27 to 3.32.

8. The tablet according to claim 1, wherein the value obtained by dividing the radius of curvature $R_3$ of the third curved surface by the radius of curvature $R_2$ of the second curved surface is within the range of 0.88 to 0.97.

9. The tablet according to claim 1, wherein the value obtained by dividing the cup depth, which is the height dimension of the cup portion, by the diameter or long axis of the tablet is within the range of 0.14 to 0.18.

10. The tablet according to claim 1, wherein the value obtained by dividing the distance from a first inflection point, which is the boundary between the first curved surface and the second curved surface, to an end of the side portion by the diameter or long axis of the tablet is within the range of 0.033 to 0.067.

11. The tablet according to claim 1, wherein the value obtained by dividing the distance from a second inflection point, which is the boundary between the second curved surface and the third curved surface, to an end of the side portion by the diameter or long axis of the tablet is within the range of 0.33 to 0.34.

12. The tablet according to claim 1, wherein the diameter or long axis is within the range of 6.0 mm to 10.5 mm.

13. The tablet according to claim 1, wherein the apparent density of an uncoated tablet composing the tablet is within the range of 1.1 mg/mm$^3$ to 1.4 mg/mm$^3$.

14. The tablet according to claim 1, wherein the value obtained by dividing the cup depth, which is the height dimension of the cup portion, by the diameter or long axis of the tablet is within the range of 0.13 to 0.18.

15. The tablet according to claim 1, wherein the value obtained by dividing the distance from a first inflection point located at the boundary between the first curved surface and the second curved surface to an end of the side portion by the diameter or long axis of the tablet is within the range of 0.030 to 0.067.

16. The tablet according to claim 1, wherein the value obtained by dividing the distance from a second inflection point located at the boundary between the second curved surface and the third curved surface to an end of the side portion by the diameter or long axis of the tablet is within the range of 0.25 to 0.40.

17. The tablet according to claim 1, wherein the diameter or long axis is within the range of 6.0 mm to 10.5 mm.

18. The tablet according to claim 1, wherein the apparent density of an uncoated tablet composing the tablet is within the range of 1.1 mg/mm$^3$ to 1.4 mg/mm$^3$.

19. The tablet according to claim 1, wherein the surface of an uncoated tablet composing the tablet is coated.

20. The tablet according to claim 19, wherein the surface of an uncoated tablet composing the tablet is coated with a film.

* * * * *